(12) United States Patent
Taverna et al.

(10) Patent No.: US 11,913,938 B2
(45) Date of Patent: Feb. 27, 2024

(54) METHODS TO ASSESS THE RISK OF BEING AFFECTED BY PROSTATE CANCER

(71) Applicants: HUMANITAS MIRASOLE S.P.A., Rozzano (IT); POLITECNICO DI MILANO, Milan (IT)

(72) Inventors: Gianluigi Taverna, Rozzano (IT); Fabio Grizzi, Rozzano (IT); Laura Maria Teresa Capelli, Milan (IT); Carmen Bax, Milan (IT); Selena Sironi, Milan (IT); Lidia Giuseppina Eusebio, Milan (IT)

(73) Assignees: HUMANITAS MIRASOLE S.P.A., Rozzano (IT); POLITECNICO DI MILANO, Milan (IT)

( * ) Notice: Subject to any disclaimer, the term of this patent is extended or adjusted under 35 U.S.C. 154(b) by 344 days.

(21) Appl. No.: 17/435,941

(22) PCT Filed: Mar. 3, 2020

(86) PCT No.: PCT/EP2020/055555
§ 371 (c)(1),
(2) Date: Sep. 2, 2021

(87) PCT Pub. No.: WO2020/178284
PCT Pub. Date: Sep. 10, 2020

(65) Prior Publication Data
US 2022/0146493 A1    May 12, 2022

(30) Foreign Application Priority Data

Mar. 5, 2019 (EP) .................... 19160856

(51) Int. Cl.
G01N 33/493 (2006.01)
G01N 27/12 (2006.01)
G01N 33/574 (2006.01)

(52) U.S. Cl.
CPC ........... *G01N 33/493* (2013.01); *G01N 27/12* (2013.01); *G01N 33/57434* (2013.01)

(58) Field of Classification Search
CPC . G01N 33/57434; G01N 33/493; G01N 27/12
See application file for complete search history.

(56) References Cited

U.S. PATENT DOCUMENTS 8,785,924 B2 * 7/2014 Jang ................. B82Y 15/00
257/253
9,285,332 B2 * 3/2016 Jang .................. G01N 27/127
(Continued)

OTHER PUBLICATIONS

Dentoni et al. "Development of an Electronic Nose for Environmental Odour Monitoring" Sensors. 2012; 12(11):14363-14381. https://doi.org/10.3390/s121114363 (Year: 2012).*

(Continued)

*Primary Examiner* — Jonathan M Dunlap
(74) *Attorney, Agent, or Firm* — NIXON & VANDERHYE

(57) ABSTRACT

Disclosed are methods for assessing the risk that a male subject is affected by prostate cancer and to methods for assessing the risk that such cancer is aggressive, by analysing the gaseous headspace of urine samples with at least three metal oxide semiconductor-based gas sensors, wherein the metal oxide of the first gas sensor is pure or doped $SnO_2$, the metal oxide of the second sensor is pure or doped ZnO and the metal oxides of the third sensor are pure or doped $SnO_2$, pure or doped $TiO_2$ and pure or doped $Nb_2O_5$.

20 Claims, 4 Drawing Sheets

(56) References Cited

U.S. PATENT DOCUMENTS 10,914,702 B2* 2/2021 Schreivogel ......... G01N 27/221
11,275,077 B2* 3/2022 Horvath .................. G01N 1/22

OTHER PUBLICATIONS

International Search Report and written Opinion of the ISA for PCT/EP2020/055555 dated May 14, 2020, 11 pages.
Aggio et al., "The use of a gas chromatography-sensor system combined with advanced statistical methods, towards the diagnosis of urological malignancies", Journal of Breath Research, vol. 10, No. 1, 017106, Feb. 11, 2016, 17 pages, XP055272069.
Aggio et al., "The use of a gas chromatography-sensor system combined with advanced statistical methods, towards the diagnosis of urological malignancies", Journal of Breath Research, vol. 10, No. 1, 017106, Sep. 1, 2016, 35 pages.
Anastasiadis et al., "Complications of prostate biopsy," Expert Rev Anticancer Ther., vol. 13, No. 7, 2013, pp. 829-837.
Asimakopoulos et al., "Prostate cancer diagnosis through electronic nose in the urine headspace setting: a pilot study," Prostate Cancer and Prostatic Diseases, vol. 17, No. 2, Apr. 1, 2014, pp. 206-211, XP055582798.
Bax et al., "Innovative Diagnostic Methods for Early Prostate Cancer Detection through Urine Analysis: A Review," Cancers, vol. 10, 2018, 29 pages, XP055582792.
Bernabei et al., "A preliminary study on the possibility to diagnose urinary tract cancers by an electronic nose," Sensors and Actuators B, vol. 131, 2008, 4 pages.
Blatt et al., "Lung cancer identification by an electronic nose based on an array of MOS sensors," Proceedings of International Joint Conference on Neural Networks, Orlando, Florida, USA, Aug. 12-17, 2007, 6 pages.
Borgognone et al., "Principal component analysis in sensory analysis: covariance or correlation matrix?" Food Quality and Preference, vol. 12, 2001, pp. 323-326.
Breiman, "Random Forests," Machine Learning, vol. 45, 2001, pp. 5-32.
Capelli et al., "Application and Uses of Electronic Noses for Clinical Diagnosis on Urine Samples: A Review," Sensors, 2016, vol. 16, 23 pages.
D'Amico et al., "Detection and identification of cancers by the electronic nose," Expert Opin. Med Diagn., vol. 6, No. 3, May 2012, pp. 175-185.
D'Amico et al., "A novel approach for prostate cancer diagnosis using a gas sensor array," Procedia Engineering, vol. 47, 2012, pp. 1113-1116.
Fang et al., "Feature selection method based on mutual information and class separability for dimension reduction in multidimensional time series for clinical data," Biomedical Signal Processing and Control, vol. 21, 2015, pp. 82-89.
Godavarti et al., "Precipitated cobalt doped ZnO nanoparticles with enhanced low temperature xylene sensing properties, " Physica B: Condensed Matter, vol. 553, 2019, pp. 151-160.
Gutierrez-Osuna, "Pattern Analysis for Machine Olfaction: A Review," IEEE Sensors Journal, vol. 2, No. 3, Jun. 2002, pp. 189-202.
James et al., "Chemical Sensors for Electronic Nose Systems," Microchimica Acta, vol. 149, 2005, pp. 1-17.
Kryvenko et al., "Prostate-specific Antigen Mass Density—A Measure Predicting Prostate Cancer Volume and Accounting for Overweight and Obesity-related Prostate-specific Antigen Hemodilution," Urology, 2016, pp. 141-147.

Kursa and Rudnicki, "Feature Selection with the Boruta Package," Journal of Statistical Software, vol. 36, No. 11, Sep. 2010, 14 pages.
Lee et al., "Recent Changes in Prostate Cancer Screening Practices and Epidemiology," The Journal of Urology, vol. 198, Dec. 2017, pp. 1230-1240.
Liaw and Wiener, "Classification and Regression by randomForest," R News, vol. 2/3, Dec. 2002, pp. 18-22.
Loutfi et al., "Electronic noses for food quaility: A review," Journal of Food Engineering, vol. 144, 2015, pp. 103-111.
Matsushima et al., "Electronic Interaction between Metal Additives and Tin Dioxide in Tin Dioxide-Based Gas Sensors," Japanese Journal of Applied Physics, vol. 27, No. 10, Oct. 1988, pp. 1798-1802.
McLachlan, "Discriminant Analysis and Statistical Pattern Recognition," John Wiley & Sons, Inc., 1992, 545 pages.
Nowotny et al., "Optimal feature selection for classifying a large set of chemicals using metal oxide sensors," Sensors and Actuators B, vol. 187, 2013, pp. 471-480.
Pardo and Sberveglieri, "Comparing the performance of different features in sensor arrays," Sensors and Actuators B, vol. 123, 2007, pp. 437-443.
Presti Jr., "Does the yield of prostate cancer biopsy and repeat biopsy justify the frequency of their use?" Nature Clinical Practice Urology, vol. 5, No. 5, May 2008, pp. 246-247.
Qiu et al., "Classification and regression of ELM, LVQ and SVM for E-nose data of strawberry juice," Journal of food engineering, vol. 144, 2015, pp. 77-85.
Roine et al., "Detection of smell print differences between nonmalignant and malignant prostate cells with an electronic nose," Future Oncology, vol. 8, No. 9, Sep. 2012, 7 pages.
Roine et al., "Detection of Prostate Cancer by an Electronic Nose: A Proof of Principle Study," The Journal of Urology, vol. 192, Jul. 2014, pp. 230-235, XP029005776.
Ruiz et al., "Cr-doped TiO2 gas sensor for exhaust No. 2 Monitoring," Sensors and Actuators B, vol. 93, 2003, pp. 509-518.
Santonico et al., "Chemical sensors for prostate cancer detection oriented to non-invasive approach," Procedia Engineering, vol. 87, 2014, pp. 320-323.
Senguttuvan et al., "Gas sensing properties of lead doped tin oxide thick films," Materials Letters, vol. 61, 2007, pp. 582-584.
Siegel et al., "Cancer Statistics, 2017," CA: A Cancer Journal for Clinicians, vol. 67, No. 1, Jan./Feb. 2017, pp. 7-30.
Smith et al., "A comparative study of the analysis of human urine headspace using gas chromatography-mass spectrometry," Journal of Breath Research, vol. 2, 2008, 037022, 11 pages.
Taverna et al., "Olfactory System of Highly Trained Dogs Detects Prostate Canver in Urine Samples," The Journal of Urology, vol. 193, Apr. 2015, pp. 1382-1387.
Taverna et al., "Highly-trained dogs' olfactory system for detecting biochemical recurrence following radical prostatectomy," Clin Chem Lab Med., vol. 54, No. 3, 2016, pp. e67-e70.
Wilson and Baietto, "Applications and Advances in Electronic-Nose Technologies," Sensors, vol. 9, 2009, bp. 5099-5148.
Wilson and Baietto, "Advances in Electronic-Nose Technologies Developed for Biomedical Applications, " Sensors, vol. 11, 2011, pp. 1105-1176.
Yamazoe, "New approaches for improving semiconductor gas sensors," Sensors and Actuators B, vol. 5, 1991, pp. 7-19.
Zhang et al., "Preparation of silver-loaded titanium dioxide hedgehog-like architecture composed of hundreds of hanorods and its fast response to xylene," Journal of Colloid and Interface Science, vol. 536, 2019, pp. 215-223.

* cited by examiner

METHODS TO ASSESS THE RISK OF BEING AFFECTED BY PROSTATE CANCER

This application is the U.S. national phase of International Application No. PCT/EP2020/055555 filed Mar. 3, 2020 which designated the U.S. and claims priority to EP Patent Application No. 19160856.1 filed Mar. 5, 2019, the entire contents of each of which are hereby incorporated by reference.

This invention relates to methods for assessing the risk that a subject is affected by prostate cancer and to methods for assessing the risk that such cancer is aggressive, by analysing the gaseous headspace of urine samples with at least three metal oxide semiconductor-based gas sensors, wherein the metal oxide of the first gas sensor is pure or doped $SnO_2$, the metal oxide of the second sensor is pure or doped ZnO and the metal oxides of the third sensor are pure or doped $SnO_2$, pure or doped $TiO_2$ and pure or doped $Nb_2O_5$.

BACKGROUND OF THE INVENTION

Prostate cancer represents the second most common cancer in men globally (Siegel et al., 2017), and the fifth most frequent cancer in the world. Serum Prostate-Specific Antigen (PSA) is, currently, the most important biomarker for the detection, follow-up, and therapeutic monitoring of prostate cancer. PSA based screening for prostate cancer has had an important impact on the epidemiology of the disease. Its use has been associated with a significant reduction in prostate cancer mortality, but has also resulted in the over-diagnosis and overtreatment of indolent prostate cancer, exposing many men to treatments without benefits (Lee at al., 2017). Its low specificity and sensitivity are mainly attributable to the fact that serum PSA may also be increased in benign conditions, such as benign prostatic hyperplasia and chronic prostatitis. Additionally, serum PSA levels are affected by biologic variability that may be related to differences in androgen levels or prostate manipulation and may have distinct racial variation (Kryvenko et al., 2016). Therefore, the currently most widely practiced method for diagnosis is to subject men with increased PSA values to biopsy sampling. Not only is this procedure invasive, but it also entails a low level of accuracy (i.e. only 30% detection rate at the first biopsy) and is prone to various complications, including sepsis and death (Anastasiadis et al., 2013; Presti et al., 2008). There is thus a need for more reliable, non-invasive, method to assess the risk that a patient is affected by prostate cancer.

When it comes to assessing the risk that a prostate cancer is aggressive, the are many available methods. One very reliable method consists in the histologic classification of the tumour stage according to the TNM classification in combination with the tumour grade according to the Gleason Score (GS), but such method entails prostatectomy.

Recently, it has been demonstrated that a trained canine olfactory system can detect prostate cancer specific volatile organic compounds (VOCs) in urine samples with high estimated sensitivity and specificity (97%). This approach might have the potential to offer a noninvasive alternative to PSA sampling and prostate biopsy for detecting prostate cancer, but requires the training and housing of dogs. In addition, the results suggest that prostate cancer specific VOCs might depend on a metabolic process of the tumor. In general, odor analysis is not simple, as it entails the objectification of a sensation; however, in the last decades, specific techniques for odor characterization and measurement have been implemented and developed (Capelli et al., 2016). Sensorial techniques are based on the principle of characterizing odors referring to the sensation caused by an odorous sample directly on a panel of human assessors. Even though chemical analysis is a more consolidated method, it can turn out to be highly complex and not always effective for odor analysis. This is particularly true in the characterization of complex odors, for which it is difficult to relate the sensation provoked by an odorous mixture in humans to its chemical composition, mostly due to the highly complicated effects of odorant mixing. For these reasons, the possibility of using an electronic nose capable of reproducing the activity of the mammalian sense of smell appears as a very interesting challenge for the definition of a modern strategy for early and non-invasive diagnosis, and possibly the prognosis of a prostate cancer Metal oxide semi conductor (MOS)-based gas sensors are currently widely used in the field of odour analysis with electronic noses (James et al., 2005; Wilson and Baietto, 2009, 2011; Loutfi et al., 2015).

PRIOR ART

Recently, it has been demonstrated that a trained canine olfactory system can detect prostate cancer specific volatile organic compounds (VOCs) in urine samples with high estimated sensitivity and specificity (97%) (Taverna et al., 2015), and that the same dogs are also able to detect Biochemically Recurrent Prostate Cancer (BCR) following radical prostatectomy (Taverna et al., 2016)

Roine et al. (2012) describe how an electronic nose equipped with a $WO_3$-based sensor is able to discriminate between healthy and cancerous prostate cells.

Asimakopoulos et al. (2014), Santonico et al. (2014), Bernabei et al. (2008) and D'Amico et al. (2012a and b), describe how an electronic nose equipped with various metallo-porphyrins-based sensors can be used on urine samples to diagnose prostate cancer.

Roine et al. (2014) disclose a method to diagnose prostate cancer from urine samples headspace created by heating the urine to 37° C. and using a gas chromatographer equipped with an MOS sensor which is a composite of $SnO_2$ and ZnO.

DETAILED DESCRIPTION OF THE INVENTION

Figure 1:
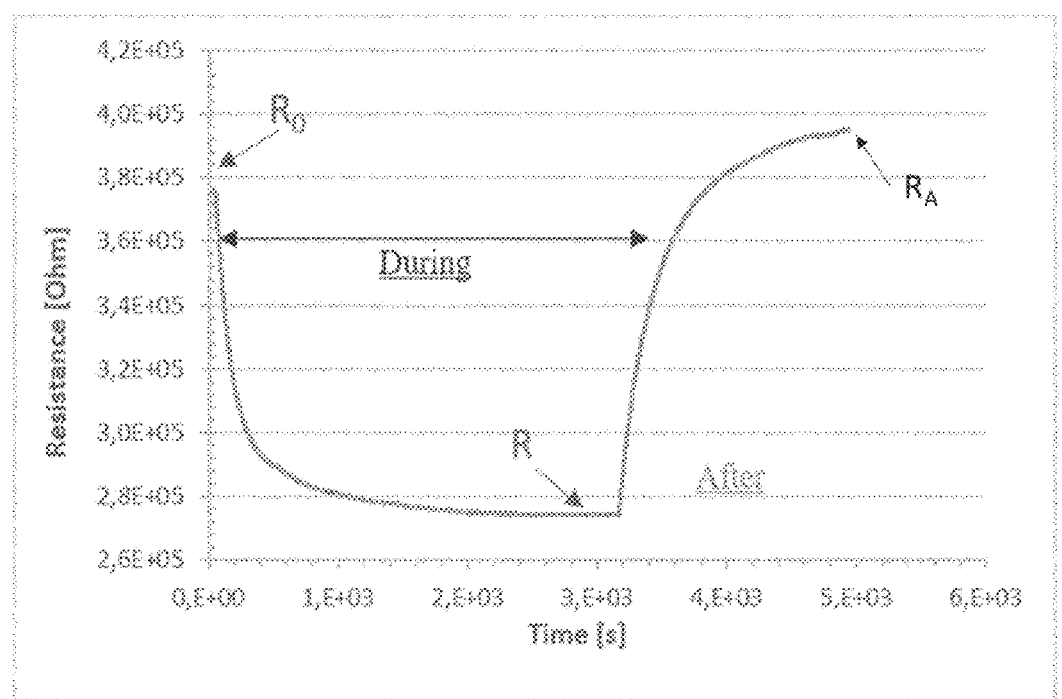
FIG. 1 Depicts a typical response curve of an MOS-based gas sensor during and after analysis of a urine headspace.

We have surprisingly found that the combined use of three types of MOS-based gas sensors allows to assess, from a urine sample of a subject, the risk that this subject is affected by a prostate cancer, so long as:

The urine sample is either collected via a catheter, or equivalent means allowing to take the sample directly from that subject's bladder, or if collected as naturally voided urine, does not comprise the last jet of that naturally voided urine, in accordance with the known literature (Smith et al., 2008)

The urine sample is heated to above 50° C. before being subjected to analysis

The analysis is performed in a humidity-controlled environment

Accordingly, in a first aspect of this invention, there is provided an in vitro method to assess risk that a subject is affected by prostate cancer, such method comprising:

a) providing a urine sample from said subject which does not comprise the last jet of a naturally voided urine sample;

b) heating the sample to above 50° C. in a closed, humidity-controlled environment;

c) analysing the headspace of the sample heated in step b), under humidity control, with at least 3 MOS-based gas sensors, wherein the metal oxide of the first gas sensor is pure or doped $SnO_2$, the metal oxide of the second sensor is pure or doped ZnO and the metal oxides of the third sensor are pure or doped $SnO_2$, pure or doped $TiO_2$ and pure or doped $Nb_2O_5$;

d) comparing the values obtained in step c) to reference values for each sensor, thereby assessing the risk that the subject is affected by prostate cancer.

In one embodiment under this first aspect of the invention, the reference values are those obtained on urine samples of subjects that have been classified as prostate cancer free or affected by prostate cancer by other means.

We have also surprisingly found that the combined use of the three types of gas sensors described above, allow to assess the risk that a prostate cancer is aggressive.

Accordingly, in a second aspect of this invention, there is provided an in vitro method to assess the risk that a subject is affected by an aggressive form of prostate cancer, such method comprising a) providing a urine sample from said subject which does not comprise the last jet of a naturally voided urine sample;

b) heating the sample to above 50° C. in a closed, humidity-controlled environment;

c) analysing the headspace of the sample heated in step b), under humidity control, with at least 3 MOS-based gas sensors, wherein the metal oxide of the first gas sensor is pure or doped $SnO_2$, the metal oxide of the second sensor is pure or doped ZnO and the metal oxides of the third sensor are pure or doped $SnO_2$, pure or doped $TiO_2$ and pure or doped $Nb_2O_5$;

d) comparing the values obtained in step c) to reference values for each sensor, thereby assessing the risk that a subject is affected by an aggressive form of prostate cancer.

In one embodiment under this second aspect of the invention, the reference values include those obtained on urine samples of subjects that have been classified affected by prostate cancer with a certain risk of being aggressive by other means.

In another one embodiment under this second aspect of the invention, the reference values are those obtained on urine samples of subjects that have been classified as prostate cancer free and affected by prostate cancer with a certain risk of being aggressive by other means.

As used herein, the terms "first gas sensor", "second gas sensor" and "third gas sensor" are not to be construed as the order in which the sensors are to be used in the methods of the invention, but only as a way to clearly distinguish the sensors from each other.

An electronic nose is an instrument which comprises an array of electronic chemical sensors with partial specificity and an appropriate pattern recognition (PR) system, capable of recognizing simple or complex odours.

The architecture of the electronic nose emulates the structure of the mammalian olfactory system, and thus, it is divided into the following three components:

Gas detection system: The actions of olfactory receptors are simulated by an array of sensors responding to a wide range of different odorants. When the sensors contact the odorous air to be analysed, they produce response signals.

Sensor-signal-processing system: The information from the sensors is compressed, simulating the action of the human olfactory bulb.

Odour recognition system: A sophisticated PR system identifies odours based on a previously stored dataset, simulating the processes that take place in the human brain.

Since the sensors are not specific, the electronic nose does not recognize the individual odour-generating compounds, but rather provides an olfactory signature (fingerprint) of the analysed air. To do this, the instrument must be trained.

E-nose training consists in the analysis of samples belonging to known odour classes: the sensor responses to these training samples constitute the "clusters" of the different odour classes that shall be discriminated.

The e-nose functioning relies on the principle of similarity: similar odours will produce similar sensor responses. Based on this principle, classification of an unknown sample is made by the instrument by comparing the sensor response produced by the unknown sample to the responses of the training sample. The unknown sample is then attributed to the training class to which it is most similar.

There are different mathematical methods that can be used for this purpose, belonging to the so called "multivariate statistical analysis".

The training phase is fundamental for the e-nose classification capability. If the different odour classes that constitute the training data set are well clustered, i.e. well separated from each other, this indicates a good capability of the instrument of discriminating the different odours, thus resulting in high classification accuracy.

Each e-nose sensor typically responds to volatile organic compounds with a variation in its resistance that produces a curve like the one shown in FIG. 1.

The set of curves produced by the sensors for all the analysed samples constitute the huge "raw" data from the electronic nose that need to be processed.

E-nose data processing consists of 2 fundamental steps:

1. Feature extraction and selection

2. Classification

Feature extraction and selection represents the set of operations that shall be carried out in order to extract from the sensor response curves the numerical data that can be further processed for classification.

The most typical feature that can be extracted from a curve like the one depicted in FIG. 1 is the resistance ratio between the resistance before flowing of the sample under analysis $R_0$, and the plateau value of the resistance measured during the measurement R.

Other examples of features that can be extracted are (not exhaustive) (Blatt et al., 2007):

The resistance change of sensor during measurement $$\Delta = R_0 - R$$

where $R_0$ is the resistance value in reference conditions, while R is the resistance value over time.

The ratio between the reference line and the minimum value of resistance reached during the measurement $$C = \frac{R_0}{\min(R(t))}$$

where $R_0$ is the resistance value in reference conditions, while R(t) is the resistance value over time.

The integral defined as $$I = \int R(t)/t \cdot R_0$$

where $R_0$ is the resistance value in reference conditions, while R(t) is the resistance value over time.

The closed area determined by the plot of the state graph of the measurement defined as $$x = R(t); y = dR(t)/dt$$

where R(t) is the resistance value over time.

The minimum value of resistance reached during the measurement $$S = \min(R(t))$$

where R(t) is the resistance value over time.

Since the number and type of features that can be extracted from the sensor response curves is almost unlimited, feature selection is required in order to consider those features that are effectively relevant for odour discrimination and classification. Different methods can be applied to carry out feature selection by optimization of the classification performances, such as filter and wrapper methods (Pardo et al., 2006, Nowotny et al., 2013, Fang et al., 2015).

Boruta algorithm is a feature selection tool, that provides a measure of the importance of a feature through the measurement of the loss of classification accuracy caused by a random permutation of feature values between objects (Kursa and Rudnicki, 2010). It is based on a wrapper approach built around a random forest classifier: the classifier is used as a black box returning a feature ranking. The classification is performed by voting of multiple unbiased weak classifiers, named decision trees, which are independently developed on different bagging samples of the training set. For each tree of the forest, the loss of classification accuracy is computed separately. Then, the importance of the feature in exam is computed as the ratio between the average loss of accuracy and its standard deviation, named Z score.

After feature extraction and selection, the e-nose data (sensor response curves) are converted into numerical data that can be processed by suitable algorithms for classification purposes. As previously mentioned, classification of an unknown sample is carried out by evaluating its similarity with the data relevant to the odour classes defined during the instrument training. The unknown sample will be attributed to the class to which it is evaluated as "most similar".

The easiest type of classification algorithm is the "cut-off" method, which uses a "yes/no" logic to distinguish between 2 classes: if the features relevant to the unknown sample exceed a given reference value, then the sample is attributed to one class, otherwise to the other one. In another very common algorithm (k-Nearest Neighbour (k-NN)), which can be applied for classification between more odour classes, the similarity is evaluated as Euclidean distance between the vector consisting of the selected features relevant to the unknown sample and the same vectors relevant to the training data. The sample is attributed to the class to which the smallest distance is calculated.

Linear Discriminant Analysis (LDA) and Quadratic Discriminant Analysis (QDA) are common classification algorithms used for e-nose data processing. Those methods involve the definition of a delimiter function between each pair of categories considered, based on the estimation of the probability distribution from the calibration dataset (McLachlan, 1992).

Random Forest algorithm is a more sophisticated classification model, which bases the classification on the construction of an entire forest of random uncorrelated decision trees (Breiman, 2001, Liaw and Wiener, 2002). Starting from the initial dataset, the model builds two new datasets: the "Boostrap Dataset" (BD) and the "Out Of Bootstrap Dataset" (OOB). The BD constitutes the first tree of classification forest with randomly selected samples of the original dataset. To build the tree, data are splitted at each node, using the feature providing the best classification performance at dividing samples by class of belonging. The choice of the feature is based on the comparison of the performance of various random variables, selected among all the variables present in the dataset. The tree stops growing when the last node has a worst classification performance of the samples than the previous one. Then, the OOB set, including samples of the original dataset not considered to build the classification tree, is used to test tree classification performance. This operation is repeated many times to build the entire forest. Once the forest has been created, the model can be used to classify samples from an independent dataset. The classification of unknown samples is based on the majority of vote of trees in the random forest.

Other common pattern recognition algorithms are, not limitedly (Gutierrez-Osuna, 2002, Aggio et al., 2016, Qui et al., 2015):

Support Vector Machine (SVM)
Partial Least Squares Interpretation (PLS)
Artificial Neural Networks (ANN)

In one embodiment under any aspect of this invention, the comparison of step d) comprises the scoring of the data acquired in step c) against a cut-off value for each sensor.

In one embodiment under any aspect of this invention, the comparison of step d) consists in the scoring of the data acquired in step c) against a cut-off value for each sensor.

In one embodiment under the first aspect of this invention, the comparison of step d) comprises the scoring, obtained through multivariate statistical analysis, of the data acquired in step c) against data acquired from the analysis of urine samples of subjects that have been classified as prostate cancer free or affected by prostate cancer by other means.

In one embodiment under the first aspect of this invention, the comparison of step d) consists in the scoring, obtained through multivariate statistical analysis, of the data acquired in step c) against data acquired from the analysis of urine samples of subjects that have been classified as prostate cancer free or affected by prostate cancer by other means.

In one embodiment under the first aspect of this invention, the comparison of step d) comprises the scoring, obtained through application of a pattern recognition algorithm, of the data acquired in step c) against data acquired from the analysis of urine samples of subjects that have been classified as prostate cancer free or affected by prostate cancer by other means.

In one embodiment under the first aspect of this invention, the comparison of step d) consists in the scoring, obtained through application of a pattern recognition algorithm, of the data acquired in step c) against data acquired from the analysis of urine samples of subjects that have been classified as prostate cancer free or affected by prostate cancer by other means.

In one embodiment under the second aspect of this invention, the comparison of step d) comprises the scoring, obtained through multivariate statistical analysis, of the data acquired in step c) against data acquired from the analysis of urine samples of subjects that have been classified as prostate cancer free and/or affected by prostate cancer with a certain risk of being aggressive by other means.

In one embodiment under the second aspect of this invention, the comparison of step d) consists in the scoring, obtained through multivariate statistical analysis, of the data acquired in step c) against data acquired from the analysis of urine samples of subjects that have been classified as prostate cancer free and/or affected by prostate cancer with a certain risk of being aggressive by other means.

In one embodiment under the second aspect of this invention, the comparison of step d) comprises the scoring, obtained through application of a pattern recognition algorithm, of the data acquired in step c) against data acquired from the analysis of urine samples of subjects that have been classified as prostate cancer free and/or affected by prostate cancer with a certain risk of being aggressive by other means.

In one embodiment under the second aspect of this invention, the comparison of step d) consists in the scoring, obtained through application of a pattern recognition algorithm, of the data acquired in step c) against data acquired from the analysis of urine samples of subjects that have been classified as prostate cancer free and/or affected by prostate cancer with a certain risk of being aggressive by other means.

In a particular embodiment under any aspect of this invention, the pattern recognition algorithm is selected from the list of k-Nearest Neighbour, Random Forest, Linear Discriminant Analysis, Quadratic Discriminant Analysis, Support Vector Machine, Discriminant Function Analysis, Partial Least Squares Interpretation and Artificial Neural Networks.

The skilled man will know that sensors are subject to wear and tear, so that the reference values for each given sensor used may fluctuate with use, and may need be redetermined from time to time.

The doping a metal-oxide based sensor is a common practice in the field to achieve modulation of the sensitivity of that particular sensor towards a particular volatile compound/set of volatile compounds (Godavarti et al. (2019); Matsushima et al. (1988); Ruiz et al. (2003); Senguttuvan et al. (2007); Yamazoe, (1991); Zhang et al. (2019)).

In one embodiment under any aspect of this invention, the dopant of the first sensor, where present, is selected from the list consisting of Mo, $MoO_3$, Pd, Ag, Cu, Al, Pb, Cr, and Pt.

In one embodiment under any aspect of this invention, the dopant of the second sensor, where present, is selected from the list consisting of Mo, $MoO_3$, Pd, Ag, Cu, Al, Pb, Cr, and Pt.

In one embodiment under any aspect of this invention, the dopant of the third sensor, where present, is selected from the list consisting of Mo, $MoO_3$, Pd, Ag, Cu, Al, Pb, Cr, and Pt.

In one embodiment under any aspect of this invention, the metal oxide of the first gas sensor is pure $SnO_2$.

In another embodiment under any aspect of this invention, the metal oxide of the first gas sensor is $SnO_2$ doped with $MoO_3$.

In another embodiment under any aspect of this invention, the metal oxide of the first gas sensor is $SnO_2$ doped with Mo.

In another embodiment under any aspect of this invention, the metal oxide of the second gas sensor is pure ZnO.

In another embodiment under any aspect of this invention, step c) is performed limitedly with the three gas sensors.

In another embodiment under any aspect of this invention, the urine sample is collected with a catheter.

In another embodiment under any aspect of this invention, the urine sample is the first jet of a naturally voided urine sample.

In another embodiment under any aspect of this invention, the urine sample is the intermediate jet of a naturally voided urine sample.

In one embodiment under any aspect of this invention, the temperature of step b) is selected the list of above 50° C., above 51° C., above 52° C., above 53° C., above 54° C., above 55° C., above 56° C., above 57° C., above 58° C. and above 59° C.

In another embodiment under any aspect of this invention, the temperature of step b) is selected from the list of about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C. about 110° C., and ranges comprising any such values.

In another embodiment under any aspect of this invention, the temperature of step b) is selected from the list of 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., and ranges comprising any such values.

In another embodiment under any aspect of this invention, the temperature of step b) is selected from the list of below 61° C., below 62° C., below 63° C., below 64° C., below 65° C., below 66° C., below 67° C., below 68° C., below 69° C., below 70° C., below 71° C., below 72° C., below 73° C., below 74° C., below 75° C., below 76° C., below 77° C., below 78° C., below 79° C., below 80° C., below 81° C., below 82° C., below 83° C., below 84° C., below 85° C., below 86° C., below 87° C., below 88° C., below 89° C., below 90° C., below 91° C., below 92° C., below 93° C., below 94° C., below 95° C., below 96° C., below 97° C., below 98° C., below 99° C. and below 100° C.

The skilled man in the art will be able to determine by trial and error method and without any undue burden the length of time needed to create the optimal headspace at any given temperature and humidity. In one embodiment under any aspect of this invention, the humidity-controlled environment is set at a value selected from the list of 10% RH-90% RH, any integer value falling within this range, and ranges comprising any of these integer values.

The skilled man will also, based on his own or other's experience and know-how, select the recipient in which to create the headspace.

All embodiments may be combined.

EXAMPLES

The invention is now described by means of non-limiting examples.

Materials & Methods

Samples Collection

Urine samples of 246 subjects (69 healthy (H) and 177 affected by prostate cancer (PC)) were collected with informed consent at the Humanitas Hospital of Castellanza (Varese) or at the Humanitas Hospital of Rozzano (Milano). Prostate cancer patient's samples were collected before biopsy, radical prostatectomy or transurethral resection of the prostate. Healthy subjects consisted of a mixture of pre-menstrual young women, young women (20-35 years of age), young (<28 years old) and middle aged (up to 50 years old) men without familial history of prostate cancer and with PSA<1 ng/ml and negative Digital Rectal Examination, as well as patients affected with ureteropelvic junction syndrome or benign prostatic hyperplasia.

The risk of aggressiveness of the 177 prostate cancer patients was set out against the criteria of Table 1 below

TABLE 1

| Risk of aggressiveness | | |
| --- | --- | --- |
| Low | Intermediate | High |
| GS = 3 + 3 and TNM pT1-2 | GS = 3 + 4 and TNM pT2 | GS > 3 + 4 or TNM pT3-4 |

These patients can also be seen to form two groups:
Group A: intermediate or high risk (159 patients)
Group B: low risk (18 patients)

Each PC subject furnished 4 samples: one taken via catheter, and three samples from a naturally voided urine (first jet, intermediate jet and last jet respectively), whereas Healthy (H) subjects only furnished the naturally voided urine samples.

Samples were collected in sterile containers commonly used for urine analysis and frozen immediately after collection at −20° C. until analysis.

Sample Preparation

Figure 2:
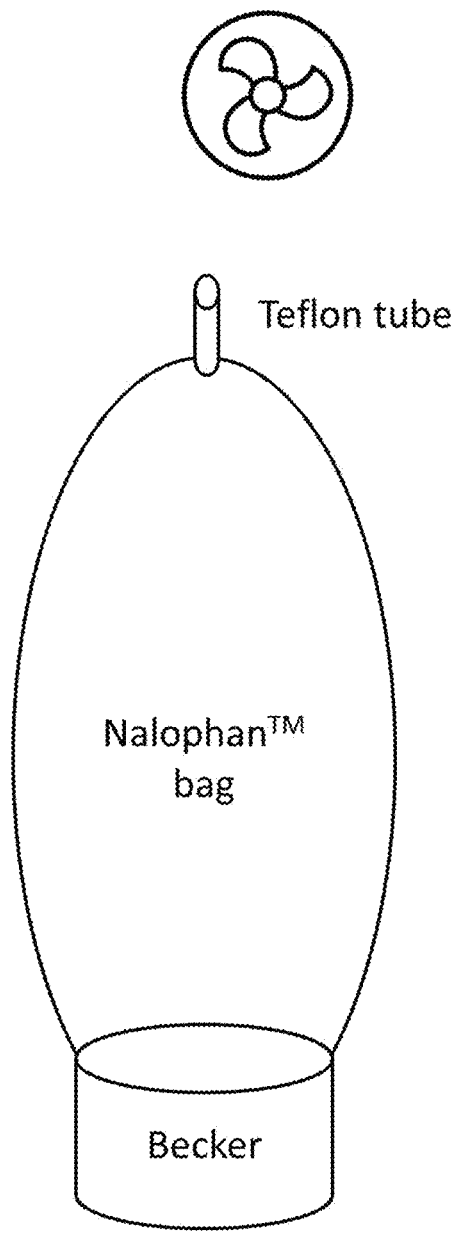
FIG. 2 Depicts a typical apparatus for the creation of the urine headspace to be analysed.

In a typical procedure, prior to being analysed, each urine sample was thawed in a water bath at 37-40° C. until completely liquid, transferred to a beaker sealed to a Nalophan™ bag equipped with a Teflon tube (FIG. 2) and kept in a climatic chamber at 60° C./60% RH for 1.5 hours, so as to create the headspace in the Nalophan™ bag for analysis with the electronic nose. The Nalophan™ bag was then separated from the beaker, sealed and the headspace so created kept at 60° C./20% RH for 2.5 h, before being flown into the electronic nose via the Teflon tube.

Headspace Analysis

The headspaces were subjected to analysis with a SACMI EOS507c electronic nose, equipped with 5 MOS-based sensors, which metal oxides are the following:
$SnO_2$ doped with cat Mo
$SnO_2$ doped with $MoO_3$
Pure $SnO_2$
Pure ZnO
$SnO_2+TiO_2+Nb_2O_5$.

Statistical Analysis

With regard to the diagnostic test in examples 1 to 6 below, the number of true positives (TP), true negatives (TN), false positives (FP) and false negatives (FN) affect the specificity, sensitivity and accuracy of the test as per the equations below, where CI 95% represents the relative confidence interval:

$$\text{Specificity} = \frac{TN}{TN+FP}$$

$$CI95\% = 1.96 * \sqrt{\frac{\text{Specificity}*(1-\text{Specificity})}{TN+FN}}$$

$$\text{Sensitivity} = \frac{TP}{TP+FN}$$

$$CI95\% = 1.96 * \sqrt{\frac{\text{Sensitivity}*(1-\text{Sensitivity})}{TP+FP}}$$

$$\text{Accuracy} = \frac{TP+TN}{TP+TN+FP+FN}$$

With regard to assessing whether a prostate cancer patient belongs to Group A or Group B as defined above, and in example 2 below the fitness of the method is determined by how the number of True Positives belonging to group A (TpA),
True Positives belonging to group B (TpB)
True positives belonging to the Healthy group (TpH)
Group A patients that are classified as Healthy (eAH)
Group B patients that are classified as Healthy (eBH)
Group A patients that are classified as Group B patients (eAB)
Group B patients that are classified as Group A patients (eBA)
Healthy subjects that are classified as Group A patients (eHA)
Healthy subjects that are classified as Group B patients (eHB)

affect the recall values and the accuracy as set out in the equations below $$\text{Recall\_GroupA} = \frac{TpA}{TpA+eAB+eAH}$$

$$CI95\% = 1.96 * \sqrt{\frac{\text{Recall\_GroupA}*(1-\text{Recall\_GroupA})}{TpA+eAB+eSA}}$$

$$\text{Recall\_GroupB} = \frac{TpB}{TpB+eBA+eBH}$$

$$CI95\% = 1.96 * \sqrt{\frac{\text{Recall\_GroupB}*(1-\text{Recall\_GroupB})}{TpB+eAB+eHB}}$$

-continued $$\text{Recall\_Healthy} = \frac{TpS}{TpS + eHA + eHB}$$

$$CI95\% = 1.96 * \sqrt{\frac{\text{Recall\_Heatlhy} * (1 - \text{Recall\_Healthy})}{TpH + eAH + eBH}}$$

$$\text{Accuracy} = \frac{TpA + TpB + TpS}{TpA + eBA + eHA + TpB + eAB + eHB + eAH + eBH + TpH}$$

With regard to assessing whether a prostate cancer patient is at high risk or intermediate risk of being affected by an aggressive form of prostate cancer in example 4 below, the fitness of the method is determined by how the number of True Positives belonging to group GS 3+4 ($TP_{Medium}$)

True positives belonging to group GS 4 ($Tp_{High}$)

Group GS 3+4 patients that are classified as group GS 4 ($e_{Medium,High}$)

Group GS 4 subjects that are classified as group GS 3+4 ($e_{High,Medium}$) affect the recall values and the accuracy as set out in the equations below $$\text{Recall}_{GS3+4} = \frac{Tp_{Medium}}{Tp_{Medium} + e_{Medium,High}}$$

$$CI95\% = 1.96 * \sqrt{\frac{\text{Recall}_{GS3+4} * (1 - \text{Recall}_{GS3+4})}{Tp_{Medium} + e_{Medium,High}}}$$

$$\text{Recall}_{GS\,4} = \frac{Tp_{High}}{Tp_{High} + e_{High,Medium}}$$

$$CI95\% = 1.96 * \sqrt{\frac{\text{Recall}_{GS4} * (1 - \text{Recall}_{GS4})}{Tp_{High} + e_{Medium,High}}}$$

$$\text{Accuracy} = \frac{Tp_{Medium} + Tp_{High}}{Tp_{Medium} + e_{Medium,High} + Tp_{High} + e_{High,Medium}}$$

Example 1: Assessing Risk of being Affected by Prostate Cancer with Cut-Off Value The first jet samples of the 246 subjects described above were subjected to the analysis as described in the material and methods section above.

Table 2 reports the accuracy, sensitivity and specificity of the test, depending on the number of sensors used and the method used to assign a subject as healthy (H) or affected by prostate cancer (PC). Entries 12 and 13 represent the values obtained by using the method of the invention.

Similar results are obtained by analysing either the intermediate jet of a naturally voided urine sample or samples taken with a catheter.

TABLE 2

| Entry | N. of sensors | Sensors used | Method | H vs PC Accuracy | Sensitivity | Specificity |
|---|---|---|---|---|---|---|
| 1 | 1 | $SnO_2$ doped with Mo | If $R_0/R \leq 2.5$: H; if $R_0/R > 2.5$: PC | 38% | 15% | 97% |
| 2 | 1 | $SnO_2$ doped with $MoO_3$ | If $R_0/R \leq 2.5$: H; if $R_0/R > 2.5$: PC | 33% | 7% | 99% |
| 3 | 1 | Pure $SnO_2$ | If $R_0/R \leq 2.5$: H; if $R_0/R > 2.5$: PC | 36% | 13% | 97% |
| 4 | 1 | Pure ZnO | If $R_0/R \leq 2.5$: H; if $R_0/R > 2.5$ PC | 58% | 39% | 97% |
| 5 | 1 | $SnO_2 + TiO_2 + Nb_2O_5$ | If $R_0/R \leq 2.5$: H; if $R_0/R > 2.5$: PC | 59% | 50% | 84% |
| 6 | 3 | $SnO_2$ doped with Mo<br>$SnO_2$ doped with $MoO_3$<br>Pure $SnO_2$ | If all $R_0/R \leq 2.5$: H; if at least one $R_0/R > 2.5$: PC | 41% | 21% | 94% |
| 7 | 2 | $SnO_2$ doped with Mo<br>Pure ZnO | If all $R_0/R \leq 2.5$: H; if at least one $R_0/R > 2.5$: PC | 63% | 51% | 93% |
| 8 | 4 | $SnO_2$ doped with Mo<br>$SnO_2$ doped with $MoO_3$<br>Pure $SnO_2$<br>Pure ZnO | If all $R_0/R \leq 2.5$: H; if at least one $R_0/R > 2.5$: PC | 63% | 53% | 91% |
| 9 | 2 | $SnO_2$ doped with Mo<br>$SnO_2 + TiO_2 + Nb_2O_5$ | If all $R_0/R \leq 2.5$: H; if at least one $R_0/R > 2.5$: PC | 66% | 59% | 83% |
| 10 | 4 | $SnO_2$ doped with Mo<br>$SnO_2$ doped with $MoO_3$<br>Pure $SnO_2$<br>$SnO_2 + TiO_2 + Nb_2O_5$ | If all $R_0/R \leq 2.5$: H; if at least one $R_0/R > 2.5$: PC | 67% | 62% | 83% |
| 11 | 2 | Pure ZnO<br>$SnO_2 + TiO_2 + Nb_2O_5$ | If all $R_0/R \leq 2.5$: H; if at least one $R_0/R > 2.5$: PC | 71% | 66% | 84% |
| 12 | 3 | Pure ZnO<br>$SnO_2$ doped with Mo<br>$SnO_2 + TiO_2 + Nb_2O_5$ | If all $R_0/R \leq 2.5$: H; if at least one $R_0/R > 2.5$: PC | 76% | 73% | 84% |
| 13 | 5 | Pure ZnO<br>$SnO_2$ doped with Mo<br>$SnO_2$ doped with $MoO_3$<br>Pure $SnO_2$<br>$SnO_2 + TiO_2 + Nb_2O_5$ | If all $R_0/R \leq 2.5$: H; if at least one $R_0/R > 2.5$: PC | 79% | 78% | 83% |

Example 2: Assessing Risk of Aggressiveness with a Cut-Off Value

The first jet samples of the 246 subjects described above were subjected to the risk of aggressiveness analysis as described in the materials and methods above. Table 3 reports the recall values and accuracy of various methods which differ by the number and types of sensor used in the analysis, and where subjects were classified as healthy or affected by prostate cancer using the corresponding method of example 1. Entries 12 and 13 represent the values obtained with the method of the invention.

Similar results are obtained by analysing either the intermediate jet of a naturally voided urine sample or samples taken with a catheter.

Figure 3:
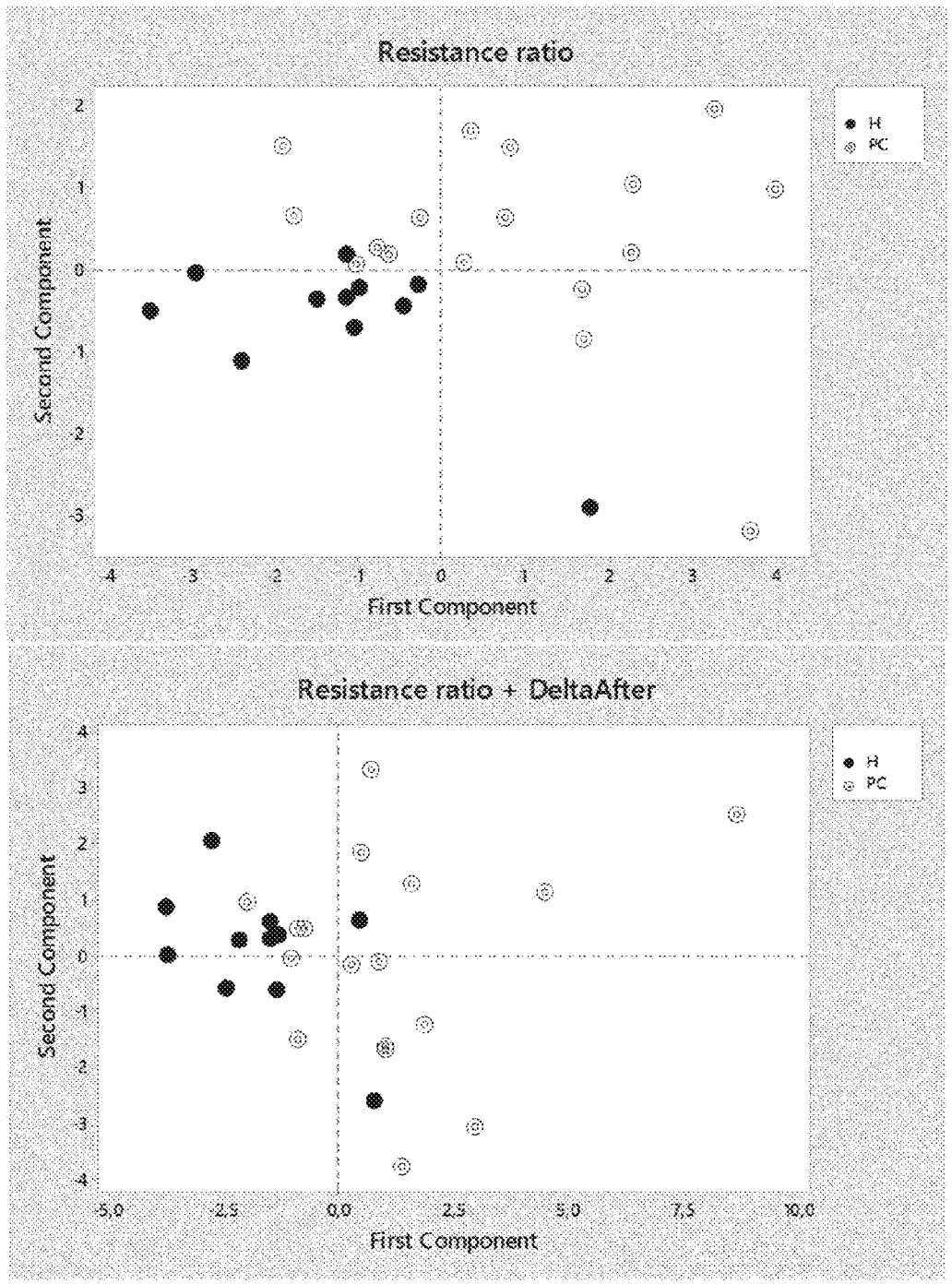
FIG. 3 Depicts two Principal Component Analysis score plots used to cluster Healthy (H) vs Prostate Cancer (PC) subjects.

As an example, FIG. 3 reports the PCA score plot obtained considering different features extracted from the sensors response curve. Different odour classes, i.e. healthy

TABLE 3

| Entry | N. of sensors | Sensors used | Method | Accuracy | Risk of aggressiveness Recall PC group A | Recall PC group B | Recall Healthy |
|---|---|---|---|---|---|---|---|
| 1 | 1 | $SnO_2$ doped with Mo | If $R_0/R > 2.5$: group B | 33% | 0% | 74% | 97% |
| 2 | 1 | $SnO_2$ doped with $MoO_3$ | If $R_0/R > 2.5$: group B | 31% | 0% | 62% | 99% |
| 3 | 1 | Pure $SnO_2$ | If $R_0/R > 2.5$: group B | 31% | 0% | 64% | 97% |
| 4 | 1 | Pure ZnO | If $R_0/R > 2.5$: group A | 57% | 43% | 0% | 97% |
| 5 | 1 | $SnO_2 + TiO_2 + Nb_2O_5$ | If $R_0/R > 2.5$: group A | 58% | 50% | 0% | 84% |
| 6 | 3 | $SnO_2$ doped with Mo $SnO_2$ doped with $MoO_3$ Pure $SnO_2$ | If at least one $R_0/R > 2.5$: group B | 34% | 0% | 83% | 94% |
| 7 | 2 | $SnO_2$ doped with Mo Pure ZnO | Highest $R_0/R$ and $R_0/R > 2.5$ for $SnO_2$-based sensor: group B Highest $R_0/R$ and $R_0/R > 2.5$ for ZnO-based sensor: group A | 60% | 44% | 71% | 93% |
| 8 | 4 | $SnO_2$ doped with Mo $SnO_2$ doped with $MoO_3$ Pure $SnO_2$ Pure ZnO | Highest $R_0/R$ and $R_0/R > 2.5$ for ZnO-based group A Highest $R_0/R$ and $R_0/R > 2.5$ for at least one of the other three sensors: group B | 59% | 44% | 71% | 91% |
| 9 | 2 | $SnO_2$ doped with Mo $SnO_2 + TiO_2 + Nb_2O_5$ | Highest $R_0/R$ and $R_0/R > 2.5$ for $SnO_2$ doped with Mo sensor: group B Highest $R_0/R$ and $R_0/R > 2.5$ for $SnO_2 + TiO_2 + Nb_2O_5$ Sensor: group A | 62% | 51% | 71% | 83% |
| 10 | 4 | $SnO_2$ doped with Mo $SnO_2$ doped with $MoO_3$ Pure $SnO_2$ $SnO_2 + TiO_2 + Nb_2O_5$ | Highest $R_0/R$ and $R_0/R > 2.5$ for $SnO_2 + TiO_2 + Nb_2O_5$ Sensor: group A Highest $R_0/R$ and $R_0/R > 2.5$ for any of the other 3 sensors: group B | 62% | 51% | 71% | 83% |
| 11 | 2 | Pure ZnO $SnO_2 + TiO_2 + Nb_2O_5$ | If $R_0/R > 2.5$ for at least one of the sensors: group A | 71% | 68% | 0% | 84% |
| 12 | 3 | Pure ZnO $SnO_2$ doped with Mo $SnO_2 + TiO_2 + Nb_2O_5$ | Highest $R_0/R$ and $R_0/R > 2.5$ for $SnO_2$ doped with Mo: group B Highest $R_0/R$ and $R_0/R > 2.5$ for at least one of the other two sensors: group A | 73% | 69% | 72% | 84% |
| 13 | 5 | Pure ZnO $SnO_2$ doped with Mo $SnO_2$ doped with $MoO_3$ Pure $SnO_2$ $SnO_2 + TiO_2 + Nb_2O_5$ | Highest $R_0/R$ and $R_0/R > 2.5$ for at least one of pure ZnO or $SnO_2 + TiO_2 + Nb_2O_5$ sensors: group A Highest $R_0/R$ and $R_0/R > 2.5$ for at least one of the other three sensors: group B | 73% | 69% | 73% | 83% |

Example 3: Assessing Risk of being Affected by Prostate Cancer Using Various Pattern Recognition Algorithms Data relevant to a subset of the 246 subjects (11 Healthy, 17 affected by prostate cancer) were processed by extracting the following features (F), with reference to FIG. 1 for the $R_0$, R and $R_A$ values:
Resistance Ratio $R_0/R$
Delta After $\delta = R_A - R$ (where $R_A$ is the resistance value recorded at the end of the measurement, see FIG. 1)
Single point is the minimum value of resistance reached during the measurement $S = \min(R(t))$ where $R(t)$ is the resistance value over time.
These data were acquired using the following set of sensors:
Pure ZnO
$SnO_2$ doped with Mo
$SnO_2$ doped with $MoO_3$
Pure $SnO_2$
$SnO_2 + TiO_2 + Nb_2O_5$
The datasets obtained from sample analysis after feature extraction were processed by Principal Component Analysis (PCA, Borgognone et al., 2001) to visualize discrimination between healthy subjects and patients affected by prostate cancer.

subjects and patients affected by prostate cancers clearly form clusters in different areas of the plot.

As a second step, different classification algorithms (A) were applied in order to perform classification on the training datasets. As an example, the different training sets were processed by Support Vector Machine (SVM) and Linear Discriminant Analysis (LDA) to evaluate test performances. Results obtained for accuracy, sensitivity and specificity as defined in the materials and methods above are reported in Table 4.

TABLE 4

| Feature and classification algorithm considered | Diagnosis performance | | |
|---|---|---|---|
| | Specificity | Accuracy | Sensitivity |
| Resistance ratio (F) + Cut-off method (A) | 96.4% | 90.9% | 100.0% |
| Resistance ratio (F) + SVM (A) | 89.3% | 90.9% | 88.2% |
| Resistance ratio (F) + LDA (A) | 82.1% | 100.0% | 70.6% |
| DeltaAfter (F) + SVM (A) | 82.1% | 72.7% | 88.2% |
| DeltaAfter (F) + LDA (A) | 85.7% | 90.9% | 82.4% |
| Single point (F) + SVM (A) | 75.0% | 72.7% | 76.5% |
| Single point (F) + LDA (A) | 78.6% | 72.7% | 82.4% |

Although the cut-off method provides the best results in terms of accuracy and sensitivity, also other classification techniques proved to be capable of providing acceptable results for prostate cancer diagnosis.

Example 4: Discrimination Between High and Medium Risk of Aggressiveness

Data relevant to a subset of the 246 subjects, including only patients affected by prostate cancer (20 patients), classified according to table 1 as being at high or intermediate risk, were processed considering the following feature:

Resistance Ratio $R_0/R$ where $R_0$ is the resistance value at the beginning of the e-nose analysis and R is the minimum resistance value recorded during the analysis of the urine headspace.

Figure 4:
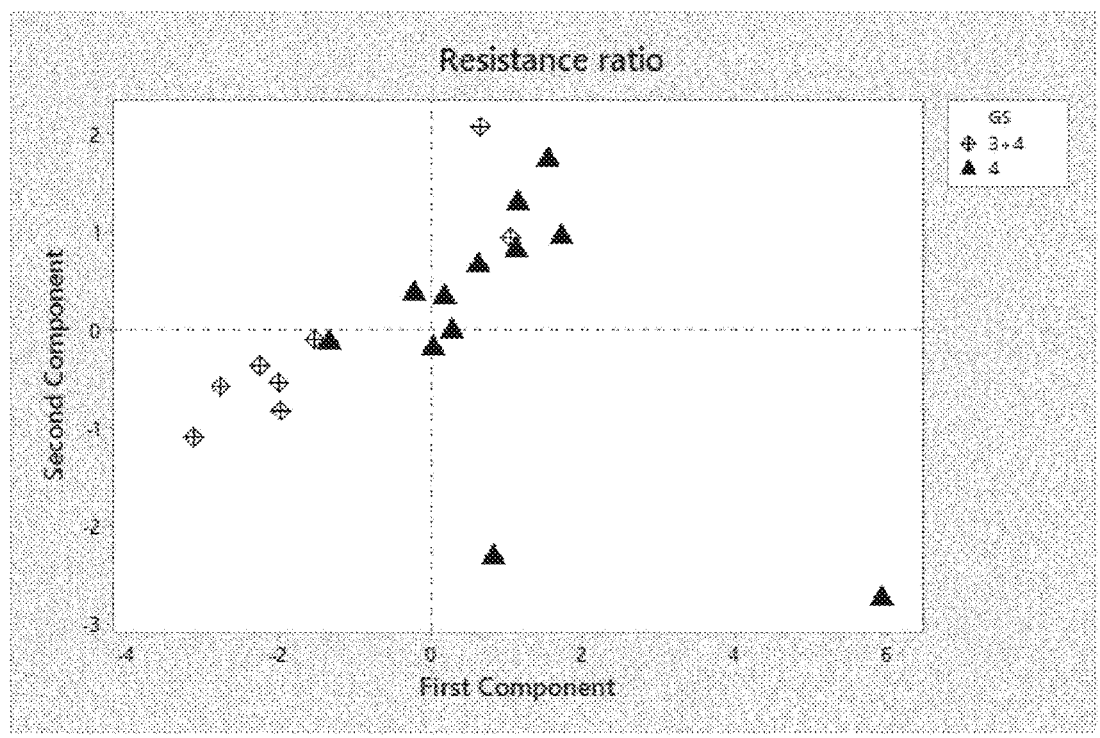
FIG. 4 Depicts a Principal Component Analysis score plot used to cluster high tumour aggressiveness (GS 4) vs intermediate tumour aggressiveness (GS 3+4) prostate cancer patients.

These data were acquired using the following set of sensors:

Pure ZnO
$SnO_2$ doped with Mo
$SnO_2$ doped with $MoO_3$
Pure $SnO_2$
$SnO_2+TiO_2+Nb_2O_5$ FIG. 4 reports the PCA score plot obtained considering the resistance ratios of the sensors as feature. The analysed samples cluster in different regions of the graph according to the Gleason Score values: Samples with a GS 3+4 cluster in the left part of the graph, whereas those with higher GS are prevailingly in the right part of it.

For the second step (classification), an SVM algorithm was applied. Thus, the data processing combination applied in this case is: resistance ratio (F)+SVM (A).

The confusion matrix relevant to the classification operated by the e-nose with this combination of feature and classification algorithm and the corresponding values of accuracy and recall are reported in Tables 5 and 6, respectively.

TABLE 5

|  |  | GS real | |
| --- | --- | --- | --- |
|  |  | 3 + 4 | 4 |
| E-nose Output | 3 + 4 | 6 | 1 |
|  | 4 | 2 | 11 |

TABLE 6

|  | Risk assessment | | |
| --- | --- | --- | --- |
| Feature and classification algorithm considered | Accuracy | Recall GS 3 + 4 | Recall GS 4 |
| Resistance ratio (F) + SVM (A) | 85 | 75 | 91.7 |

Example 5: Effect of Temperature

Tables 7 and 8 below, report the statistical values obtained when the methods of diagnosis (table 7) or prognosis (table 8) of the invention (entries 13 of examples 1 and 2) compared to those obtained when the sample is kept at 50° C. rather than 60° C.

The data at 50° C. was acquired on a subset of the 246 subjects (19 Healthy, 29 group A patients, 6 group B patients)

TABLE 7

| Healthy H vs PC | 50° C. | 60° C. |
| --- | --- | --- |
| Accuracy | 74% | 79% |
| Sensitivity | 69% | 78% |
| Specificity | 84% | 83% |

TABLE 8

| Staging PCa | 50° C. | 60° C. |
| --- | --- | --- |
| Accuracy | 56% | 73% |
| Recall PC Group A | 28% | 69% |
| Recall PC Group B | 100% | 73% |
| Recall Healthy | 84% | 83% |

Example 6: Effect of Humidity Control

Table 9 below reports the statistical values obtained when using the sensors of entry 13 of example 1, where the urine headspace enrichment and the analysis with the electronic nose is carried out under humidity control as per method of the invention, compared to those obtained when the urine headspace after the enrichment is analysed in the same conditions but without any humidity control.

Samples considered for this evaluation constitute a subset of the 246 subjects (5 healthy, 5 group A patients). Using this subset, with the sensors of entry 13 of example 1, the cut off values are as follows:

Pure ZnO: 2.5
$SnO_2$ doped with Mo: 2.5
$SnO_2$ doped with $MoO_3$: 2.5
Pure $SnO_2$: 2.5
$SnO_2+TiO_2+Nb_2O_5$:4.1

TABLE 9

| Healthy H vs PC | Without humidity control | With humidity control |
| --- | --- | --- |
| Accuracy | 30% | 100% |
| Sensitivity | 60% | 100% |
| Specificity | 0% | 100% |

Example 7: Assessing Risk of being Affected by Prostate Cancer Using Various Pattern Recognition Algorithms Data relevant to a subset of the 246 subjects, including 38 subjects (14 controls, 24 men affected by prostate cancer) were acquired using the following set of sensors:

Pure ZnO
$SnO_2$ doped with Mo
$SnO_2$ doped with $MoO_3$
Pure $SnO_2$
$SnO_2+TiO_2+Nb_2O_5$ Data were processed by extracting the following features, with reference to FIG. 1 for the $R_0$ and R values, which were used to build the training set:

Ratio between $R_0$ and R;
Difference between $R_0$ and R;
The area under the curve R(t) defined by the integral $$I = \int R(t)/t \cdot R_0$$

where $R_0$ is the resistance value in reference conditions, while R(t) is the resistance value over time recorded during the desorption of volatile organic compounds (i.e. After);

Slope of the resistance curve R(t) relevant to the adsorption phase of volatile organic compounds (i.e. During);

Difference between the resistance value recorded at the central point of the During phase and the resistance value recorded at the end of the During phase.

As a second step, different classification algorithms were applied in order to perform classification on the training dataset. As an example, the different training sets were processed by k-Neirest Neighbour (k-NN) and Random Forest (RF) to evaluate test performances. The confusion matrix relevant to the classifications operated by the e-nose with the combination of feature above-listed and classification algorithms are reported in Table 10 and Table 11, respectively for RF and k-NN models. Results obtained for accuracy, sensitivity and specificity are reported in Table 12.

TABLE 10

|  |  | E-nose output | |
|---|---|---|---|
|  |  | Healthy | Sick |
| Clinical condition | Healthy | 12 | 2 |
|  | Sick | 3 | 21 |

TABLE 11

|  |  | E-nose output | |
|---|---|---|---|
|  |  | Healthy | Sick |
| Clinical condition | Healthy | 12 | 2 |
|  | Sick | 7 | 17 |

TABLE 12

| Classification algorithm considered | Diagnosis performance | | |
|---|---|---|---|
|  | Accuracy | Specificity | Sensitivity |
| k-NN (k = 3) | 78% ± 14% | 86% ± 16% | 71% ± 20% |
| Random Forest | 87% ± 11% | 86% ± 9% | 88% ± 7% |

Accuracy, sensitivity and specificity are defined as follows, with reference to Table 13:

$$\text{Specificity} = \frac{TN}{TN + FP}$$

$$CI95\%_{Specificity} = 1.96 * \sqrt{\frac{Specificity * (1 - Specificity)}{TN + FN}}$$

$$\text{Sensitivity} = \frac{TP}{TP + FN}$$

$$CI95\%_{Sensitivity} = 1.96 * \sqrt{\frac{Sensitivity * (1 - Sensitivity)}{TP + FP}}$$

$$\text{Accuracy} = \frac{TP + TN}{TP + TN + FN + FP}$$

$$CI95\%_{Accuracy} = 1.96 * \sqrt{\frac{Accuracy * (1 - Accuracy)}{TP + TN + FN + FP}}$$

TABLE 13

|  |  | E-nose output | |
|---|---|---|---|
|  |  | Healthy | Sick |
| Clinical condition | Healthy | TN | FP |
|  | Sick | FN | TP |

Example 8: Discrimination Between High and Intermediate Risk of Aggressiveness

Data relevant to a subset of the 246 subjects, including only patients affected by prostate cancer (24 patients), classified according to Table 1 as being at high or intermediate risk, were processed considering the following features, with reference to FIG. 1 for the $R_0$ and R values, to build the training set:

Ratio between $R_0$ and R;

Difference between $R_0$ and R;

The area under the curve R(t) defined by the integral $$I = \int R(t)/t \cdot R_0$$

where $R_0$ is the resistance value in reference conditions, while R(t) is the resistance value over time recorded during the desorption of volatile organic compounds (i.e. After);

Slope of the resistance curve R(t) relevant to the adsorption phase of volatile organic compounds (i.e. During);

Difference between the resistance value recorded at the central point of the During phase and the resistance value recorded at the end of the During phase.

Data were acquired using the following set of sensors:

Pure ZnO $SnO_2$ doped with Mo $SnO_2$ doped with $MoO_3$

Pure $SnO_2$ $SnO_2 + TiO_2 + Nb_2O_5$

For classification, k-Nearest Neighbour (k-NN) and Random Forest (RF) classification algorithms were applied in order to perform classification on the training dataset. The confusion matrix relevant to the classifications operated by the e-nose with the combination of feature above-listed and classification algorithms are reported in Table 14 and 15, respectively for RF and k-NN models. The corresponding values of accuracy and recall relevant to the classification operated by the e-nose with this combination of features and classification algorithms are reported in Table 16.

TABLE 14

|  |  | E-nose output | |
|---|---|---|---|
|  |  | High | Intermediate |
| Clinical condition | High | 12 | 1 |
|  | Intermediate | 1 | 10 |

TABLE 15

|  |  | E-nose output | |
|---|---|---|---|
|  |  | High | Intermediate |
| Clinical condition | High | 12 | 1 |
|  | Intermediate | 3 | 8 |

TABLE 16

| Classification algorithm considered | Prostate cancer risk assessment | | |
|---|---|---|---|
|  | Accuracy | Recall$_{Intermediate}$ | Recall$_{High}$ |
| k-NN (k = 1) | 83% ± 15% | 73% ± 15% | 92% ± 7% |
| Random Forest | 92% ± 11% | 91% ± 9% | 92% ± 7% |

Recall and accuracy are determined as follows with reference to Table 17:

$$Recall_{Intermediate} = \frac{Tp_{Intermediate}}{Tp_{Intermediate} + e_{Intermediate,High}}$$

$$CI95\%_{Recall_{Intermediate}} = 1.96 * \sqrt{\frac{Recall_{Intermediate} * (1 - Recall_{Intermediate})}{Tp_{Intermediate} + e_{High,Intermediate}}}$$

$$Recall_{High} = \frac{Tp_{High}}{Tp_{High} + e_{High,Intermediate}}$$

$$CI95\%_{Recall_{High}} = 1.96 * \sqrt{\frac{Recall_{High} * (1 - Recall_{High})}{Tp_{High} + e_{Intermediate,High}}}$$

$$Accuracy = \frac{Tp_{Intermediate} + Tp_{High}}{Tp_{Intermediate} + e_{Intermediate,High} + Tp_{High} + e_{High,Intermediate}}$$

$$CI95\%_{Accuracy} = 1.96 * \sqrt{\frac{Accuracy * (1 - Accuracy)}{Tp_{Intermediate} + e_{Intermediate,High} + Tp_{High} + e_{High,Intermediate}}}$$

TABLE 17

|  |  | EN Classification | |
|---|---|---|---|
|  |  | High | Intermediate |
| Clinical Condition | High | Tp$_{High}$ | e$_{High; Intermediate}$ |
|  | Intermediate | e$_{Intermediate; High}$ | Tp$_{Intermediate}$ |

REFERENCES

Aggio et al., (2016), J Breath Res.; 10(1):017106. doi: 10.1088/1752-7155/10/1/017106.
Anastasiadis et al. Expert Rev Anticancer Ther 2013; 13: 829.
Asimakopoulos et al. (2014), Prostate Cancer Prostatic Dis. 2014 June; 17(2):206-11. doi: 10.1038/pcan.2014.11.
Bernabei et al. (2008), Sensors and Actuators B: Chemical Volume 131, Issue 1, 14 Apr. 2008, Pages 1-4.
Blatt et al. (2007), Lung cancer identification by an electronic nose based on an array of MOS sensors. 2007 International Joint Conference on Neural Networks, Orlando, Fla., pp. 1423-1428.
Borgognone et al. (2001), Food Quality and Preference, 2, 323-326.
Breiman, Machine Learning 2001, 45, 5-32.
Capelli et al. (2016), Sensors (Basel). 2016; 16(10): 1708.
D'Amico et al. (2012a), Expert Opin Med Diagn. 2012 May; 6(3):175-85. doi: 10.1517/17530059.2012.665870.
D'Amico et al. (2012b), Procedia Engineering, Volume 47, 2012, Pages 1113-1116.
Fang et al. (2015), Biomedical Signal Processing and Control, Volume 21, 2015, Pages 82-89.
Godavarti et al. (2019). Physica B: Condensed Matter 553: 151-160.
Gutierrez-Osuna (2002), Pattern analysis for machine olfaction: a review. IEEE Sensors Journal, 2, 189-202.
James et al., 2005, Microchimica Acta, vol 149, pages 1-17.
Kryvenko et al. (2016), The Journal of Urology. 2016; 196(6):1659-1663.
Kursa and Rudnicki, Journal Of Statistical Software 2010, 36 (11).
Lee at al. (2017), The Journal of Urology. 2017; 198(6): 1230-1240.
Liaw and Wiener, R News 2002, 2/3, 18.
Loutfi et al., 2015, Journal of Food Engineering, vol 144, pages 103-111.
McLachlan. G. J., Discriminant Analysis and Statistical Pattern Recognition. John Wiley & Sons, Inc: Hobokenn N.J., 1992 Matsushima et al. (1988) Japanese Journal of Applied Physics 27(Part 1, No. 10): 1798-1802.
Nowotny et al. (2013), Sensors and Actuators B: Chemical, 187, 471-480.
Pardo et al. (2006), Sensors and Actuators B, 123, 437-443.
Presti et al. (2008), Nat Clin Pract Urol 5: 246.
Qui et al. (2015), Journal of food engineering, 144, 77-85.
Roine et al. (2012), Future Oncol. 2012 September; 8(9): 1157-65. doi: 10.2217/fon.12.93.
Roine et al. (2014), Journal of Urology, 192, 230-235.
Ruiz, A. M., et al. (2003). Sensors and Actuators B:Chemical 93(1): 509-518.
Santonico et al. (2014), Procedia Engineering, Volume 87, 2014, Pages 320-323.
Senguttuvan, T. D., et al. (2007), Materials Letters 61(2): 582-584.
Siegel et al. (2017), CA: A Cancer Journal for Clinicians. 2017; 67(1): 7-30.
Smith et al. (2008), J Breath Res. 2008 September; 2(3): 037022. doi: 10.1088/1752-7155/2/3/03702.
Taverna et al. (2015) The Journal of Urology. 2015; 193(4): 1382-1387.
Taverna et al. (2016), Clin Chem Lab Med. 2016; 54(3): e67-70.
Wilson and Baietto, 2009, Sensors, 9(7), pp. 5099-5148.
Wilson and Baietto, 2011, Sensors, 11(1), pp. 1105-1176.
Yamazoe, N. (1991) Sensors and Actuators B:Chemical 5(1): 7-19.
Zhang, Y., et al. (2019) Journal of Colloid and Interface Science 536: 215-223.

The invention claimed is:

1. An in vitro method to assess the risk that a subject is affected by prostate cancer, such method comprising:
  a) providing a urine sample from said subject which does not comprise the last jet of a naturally voided urine sample;
  b) heating the sample to above 50° C. in a closed, humidity-controlled environment;
  c) analysing the headspace of the sample heated in step b), under humidity control, with at least 3 Metal Oxide Semiconductor (MOS)-based gas sensors, wherein the metal oxide of the first gas sensor is pure or doped $SnO_2$, the metal oxide of the second sensor is pure or doped ZnO and the metal oxides of the third sensor are pure or doped $SnO_2$, pure or doped $TiO_2$ and pure or doped $Nb_2O_5$;

d) comparing the values obtained in step c) to reference values for each sensor, thereby assessing the risk that a subject is affected by prostate cancer.

2. The method of claim 1, wherein the reference values are those obtained on urine samples of subjects that have been classified as prostate cancer free or affected by prostate cancer by other means.

3. The method of claim 2, wherein the metal oxide of the first sensor is doped with $MoO_3$.

4. The method of claim 2, wherein the metal oxide of the first sensor is doped with Mo.

5. The method of claim 1, wherein the comparison of step comprises the scoring, obtained through multivariate statistical analysis, of the data acquired in step c) against data acquired from the analysis of urine samples of subjects that have been classified as prostate cancer free or affected by prostate cancer by other means.

6. The method of claim 5, wherein the metal oxide of the first sensor is doped with $MoO_3$.

7. The method of claim 5, wherein the metal oxide of the first sensor is doped with Mo.

8. The method of claim 1, wherein the metal oxide of the first sensor is doped with $MoO_3$.

9. The method of claim 1, wherein the metal oxide of the first sensor is doped with Mo.

10. The method of claim 1, wherein the metal oxide of the second sensor is pure ZnO.

11. The method of claim 1, wherein the metal oxides of the third gas sensor are not doped.

12. The method of claim 1, wherein the dopant for any given sensor, where present, is independently selected from the list of Mo, $MoO_3$, Pd, Ag, Cu, Al, Pb, Cr, and Pt.

13. The method of claim 1, wherein the temperature of step b) is selected from the list of above 51° C., above 52° C., above 53° C., above 54° C., above 55° C., above 56° C., above 57° C., above 58° C. and above 59° C.

14. The method of claim 1, wherein the temperature of step b) is selected from the list of below 61° C., below 62° C., below 63° C., below 64° C., below 65° C., below 66° C., below 67° C., below 68° C., below 69° C., below 70° C., below 71° C., below 72° C., below 73° C., below 74° C., below 75° C., below 76° C., below 77° C., below 78° C., below 79° C., below 80° C., below 81° C., below 82° C., below 83° C., below 84° C., below 85° C., below 86° C., below 87° C., below 88° C., below 89° C., below 90° C., below 91° C., below 92° C., below 93° C., below 94° C., below 95° C., below 96° C., below 97° C., below 98° C., below 99° C. and below 100° C.

15. An in vitro method to assess the risk that a subject is affected by an aggressive form of prostate cancer, such method comprising
   a) providing a urine sample from said subject which does not comprise the last jet of a naturally voided urine sample;
   b) heating the sample to above 50° C. in a closed, humidity-controlled environment;
   c) analysing the headspace of the sample heated in step b), under humidity control, with at least 3 MOS-based gas sensors, wherein the metal oxide of the first gas sensor is pure or doped $SnO_2$, the metal oxide of the second sensor is pure or doped ZnO and the metal oxides of the third sensor are pure or doped $SnO_2$, pure or doped $TiO_2$ and pure or doped $Nb_2O_5$;
   d) comparing the values obtained in step c) to reference values for each sensor, thereby assessing the risk that a subject is affected by an aggressive form of prostate cancer.

16. The method of claim 15, wherein the reference values include those obtained on urine samples of subjects that have been classified as affected by prostate cancer with a certain risk of being aggressive by other means.

17. The method of claim 16, wherein the metal oxide of the first sensor is doped with $MoO_3$.

18. The method of claim 15, wherein the comparison of step d) comprises the scoring, obtained through multivariate statistical analysis, of the data acquired in step c) against data acquired from the analysis of urine samples of subjects that have been classified as affected by prostate cancer with a certain risk of being aggressive by other means.

19. The method of claim 18, wherein the metal oxide of the first sensor is doped with $MoO_3$.

20. The method of claim 15, wherein the metal oxide of the first sensor is doped with $MoO_3$.

* * * * *